(12) United States Patent
Ripley et al.

(10) Patent No.: US 9,987,214 B2
(45) Date of Patent: Jun. 5, 2018

(54) COMBINATIONS FOR ORAL COMPOSITIONS, THEIR PREPARATION AND USE

(71) Applicants: Oraldent Limited, Kimbolton (GB); Ricerfarma S.R.L., Milan (IT)

(72) Inventors: Ian Ripley, Kimbolton (GB); Howard Thomas, Kimbolton (GB)

(73) Assignees: Oraldent Limited, Kimbolton Cambridgeshire (GB); Ricerfarma S.R.L., Milan (IT)

( * ) Notice: Subject to any disclaimer, the term of this patent is extended or adjusted under 35 U.S.C. 154(b) by 0 days. days.

(21) Appl. No.: 15/247,806

(22) Filed: Aug. 25, 2016

(65) Prior Publication Data

US 2016/0361346 A1 Dec. 15, 2016

Related U.S. Application Data

(62) Division of application No. 12/374,443, filed as application No. PCT/GB2007/002756 on Jul. 20, 2007, now Pat. No. 9,532,939.

(30) Foreign Application Priority Data

Jul. 20, 2006 (GB) .................... 0614353.1

(51) Int. Cl.
| | |
|---|---|
| *A61K 36/752* | (2006.01) |
| *A61K 9/00* | (2006.01) |
| *A61K 31/7048* | (2006.01) |
| *A61K 31/728* | (2006.01) |
| *A61K 8/97* | (2017.01) |
| *A61K 8/362* | (2006.01) |
| *A61K 8/73* | (2006.01) |
| *A61K 8/60* | (2006.01) |
| *A61K 47/12* | (2006.01) |
| *A61Q 11/00* | (2006.01) |
| *A61K 8/365* | (2006.01) |
| *A61K 8/41* | (2006.01) |
| *A61K 8/49* | (2006.01) |
| *A61K 8/67* | (2006.01) |

(52) U.S. Cl.
CPC .............. *A61K 8/735* (2013.01); *A61K 8/362* (2013.01); *A61K 8/365* (2013.01); *A61K 8/416* (2013.01); *A61K 8/498* (2013.01); *A61K 8/602* (2013.01); *A61K 8/676* (2013.01); *A61K 8/97* (2013.01); *A61K 9/0014* (2013.01); *A61K 9/0053* (2013.01); *A61K 31/7048* (2013.01); *A61K 31/728* (2013.01); *A61K 36/752* (2013.01); *A61K 47/12* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 2,823,166 | A | 2/1958 | Hoffman |
| 2,888,381 | A | 5/1959 | Freedman et al. |
| 4,303,676 | A | 12/1981 | Balazs |
| 5,571,518 | A | 11/1996 | Pillai et al. |
| 5,728,391 | A | 3/1998 | Ikeya et al. |
| 6,120,779 | A | 9/2000 | Nayak et al. |
| 6,706,256 | B2 | 3/2004 | Lawlor |
| 2002/0114730 | A1 | 8/2002 | Jazzar |
| 2002/0155163 | A1 | 10/2002 | Benjamin et al. |
| 2003/0017219 | A1 | 1/2003 | Corsini et al. |
| 2003/0125264 | A1* | 7/2003 | Malik .................... A61K 31/35 514/27 |
| 2004/0157800 | A1 | 8/2004 | Buononato et al. |
| 2005/0215493 | A1 | 9/2005 | Miyake et al. |
| 2006/0018860 | A1 | 1/2006 | Chen et al. |
| 2006/0034784 | A1 | 2/2006 | Cahen |
| 2007/0053851 | A1 | 3/2007 | Maillan et al. |
| 2010/0047824 | A1 | 2/2010 | Suasin et al. |
| 2010/0055053 | A1 | 3/2010 | Ian et al. |
| 2010/0068157 | A1 | 3/2010 | Ripley |

FOREIGN PATENT DOCUMENTS

| | | | | |
|---|---|---|---|---|
| DE | 19949575 | A1 | 4/2001 | |
| EP | 0444492 | A1 | 9/1991 | |
| EP | 1582105 | A1 | 10/2005 | |
| EP | 1600143 | A1 * | 11/2005 | ........... A61K 8/0212 |
| EP | 1600143 | A1 | 11/2005 | |
| JP | 62-51613 | A | 3/1987 | |
| JP | 2003-073279 | A | 3/2003 | |

(Continued)

OTHER PUBLICATIONS

MB Brown*, SA Jones. Hyaluronic acid: a unique topical vehicle for the localized delivery of drugs to the skin. JEADV (2005) 19 308-318.*
Hou, JP and Jin Y. The Healing Power of Chinese Herbs and Medicinal Recipes. Binghampton, NY: The Haworth Press, 2005, pp. 204-206. (Year: 2005).*
"U.S. Appl. No. 12/374,443, Advisory Action dated Apr. 11, 2012", 3 pgs.
"U.S. Appl. No. 12/374,443, Advisory Action dated Jul. 1, 2015", 6 pgs.
"U.S. Appl. No. 12/374,443, Final Office Action dated Jan. 30, 2012", 15 pgs.
"U.S. Appl. No. 12/374,443, Final Office Action dated Dec. 5, 2014", 19 pgs.
"U.S. Appl. No. 12/374,443, Non Final Office Action dated Jan. 30, 2014", 12 pgs.
"U.S. Appl. No. 12/374,443, Non Final Office Action dated Jul. 28, 2011", 15 pgs.

(Continued)

*Primary Examiner* — Isaac Shomer
*Assistant Examiner* — Michael P Cohen
(74) *Attorney, Agent, or Firm* — Schwegman Lundberg & Woessner, P.A.

(57) ABSTRACT

A composition having a pH in the range of from 3 to 8.5, comprising: (a) in the range of from 0.1% to <10% w/w (based on the total weight of the composition) of a stock solution comprising a mixture of bioflavonoids and fruit acids or salts thereof; (b) sodium hyaluronate; and (c) water; and, optionally, (d) a pharmaceutically acceptable carrier therefor; wherein the sodium hyaluronate has an average molecular weight of between 800,000 and 4,000,000.

15 Claims, No Drawings

(56) References Cited

FOREIGN PATENT DOCUMENTS

| WO | WO-0245515 A1 | 6/2002 |
|----|---------------|--------|
| WO | WO-0247615 A2 | 6/2002 |
| WO | WO-03039452 A2 | 5/2003 |
| WO | WO-03097078 A1 | 11/2003 |
| WO | WO-2004071472 A1 | 8/2004 |
| WO | WO-2004103542 A1 | 12/2004 |
| WO | WO-2005025527 A1 | 3/2005 |
| WO | WO-2005102266 A1 | 11/2005 |
| WO | WO-2006006256 A1 | 1/2006 |
| WO | WO-2006069210 A2 | 6/2006 |

OTHER PUBLICATIONS

"U.S. Appl. No. 12/374,443, Non Final Office Action dated Nov. 13, 2015", 8 pgs.
"U.S. Appl. No. 12/374,443, Preliminary Amendment filed Jan. 20, 2009", 8 pgs.
"U.S. Appl. No. 12/374,443, Response filed May 5, 2015 to Final Office Action dated Dec. 5, 2014", 9 pgs.
"U.S. Appl. No. 12/374,443, Response filed May 13, 2016 to Non Final Office Action dated Nov. 13, 2015", 7 pgs.
"U.S. Appl. No. 12/374,443, Response filed Jun. 7, 2011 to Restriction Requirement dated May 10, 2011", 11 pgs.
"U.S. Appl. No. 12/374,443, Response filed Jul. 2, 2012 to Advisory Action dated Apr. 11, 2012", 16 pgs.
"U.S. Appl. No. 12/374,443, Response filed Jul. 30, 2014 to Non Final Office Action dated Jan. 30, 2014", 11 pgs.
"U.S. Appl. No. 12/374,443, Response filed Oct. 28, 2011 to Non Final Office Action dated Jul. 28, 2011", 13 pgs.
"U.S. Appl. No. 12/374,443, Response Filed Mar. 29, 2012 to Final Office Action dated Jan. 30, 2012", 15 pgs.
"U.S. Appl. No. 12/374,443, Restriction Requirement dated May 10, 2011", 10 pgs.
"U.S. Appl. No. 12/374,443, Supplemental Amendment Under 37 C.F.R. 1.111 filed Aug. 8, 2014", 6 pgs.
"U.S. Appl. No. 12/374,447, Response filed Jan. 11, 2016 to Final Office Action dated Jul. 9, 2015", 13 pgs.
"U.S. Appl. No. 12/374,447, Final Office Action dated Mar. 2, 2012", 17 pgs.
"U.S. Appl. No. 12/374,447, Final Office Action dated Apr. 19, 2012", 19 pgs.
"U.S. Appl. No. 12/374,447, Final Office Action dated Jul. 9, 2015", 19 pgs.
"U.S. Appl. No. 12/374,447, Non Final Office Action dated Apr. 26, 2016", 17 pgs.
"U.S. Appl. No. 12/374,447, Non Final Office Action dated Aug. 18, 2014", 20 pgs.
"U.S. Appl. No. 12/374,447, Non Final Office Action dated Aug. 23, 2011", 14 pgs.
"U.S. Appl. No. 12/374,447, Preliminary Amendment filed Aug. 4, 2014", 8 pgs.
"U.S. Appl. No. 12/374,447, Response filed Feb. 18, 2015 to Non Final Office Action dated Aug. 18, 2014", 10 pgs.
"U.S. Appl. No. 12/374,447, Response Filed Sep. 19, 2012 to Final Office Action dated Mar. 2, 2012", 18 pgs.
"U.S. Appl. No. 12/374,447, Response filed Nov. 22, 2011 to Non Final Office Action dated Aug. 23, 2011", 13 pgs.
"U.S. Appl. No. 12/374,447, Supplemental Amendment and Response to Office Action dated Aug. 18, 2014", 9 pgs.
"U.S. Appl. No. 12/374,447, Supplemental Preliminary Amendment filed Aug. 8, 2014", 6 pgs.
"Chemopharma: Soluble Citrus Extracts and Figure 1", Internet Archive, Wayback Machine [www.chemopharma.com/soluble_citrus_extracts.htm], downloaded Jul. 24, 2014, (Mar. 15, 2005), 2 pgs.
"Definition of 'pith'", [Online]. Retrieved from the Internet: <http://www.oxforddictionaries.com/definition/english/pith>, (2014)
"Grapefruit Seed Extract", http://en.wikipedia.org/wiki/Grapefruit_seed_extract, (Jun. 5, 2012), 6 pgs.
"International Application Serial No. PCT/GB2007/002756, International Preliminary Report on Patentability completed Jul. 31, 2008", 15 pgs.
"International Application Serial No. PCT/GB2007/002756, International Search Report dated Nov. 30, 2007", 4 pgs.
"International Application Serial No. PCT/GB2007/002756, Response filed May 20, 2008 to International Search Report and Written Opinion dated Nov. 30, 2007", 6 pgs.
"International Application Serial No. PCT/GB2007/002756, Written Opinion dated Nov. 30, 2007", 7 pgs.
"International Application Serial No. PCT/GB2007/002758, International Preliminary Report on Patentability dated Jul. 30, 2008", 13 pgs.
"International Application Serial No. PCT/GB2007/002758, International Search Report dated Nov. 30, 2007", 3 pgs.
"International Application Serial No. PCT/GB2007/002758, Response filed May 20, 2008 to International Search Report and Written Opinion dated Nov. 30, 2007", 7 pgs.
"International Application Serial No. PCT/GB2007/002758, Written Opinion dated Nov. 30, 2007", 7 pgs.
"Letter from Exquim, S.A.—Ferrer", (May 13, 2009), 1 pg.
"Monograph from chemopharma/Exquim", [Online]. Retrieved from the Internet:<http://web.archive.org/web/20030708200513/http.//www.chemopharma.com/soluble_citru, (accessed Jul. 7, 2011), 2 pgs.
"United Kingdom Application Serial No. GB0614353.1, Search Report dated Nov. 14, 2006", 2 pgs.
"United Kingdom Application Serial No. GB0714228.4, Combined Search and Examination Report dated Nov. 2, 2007", 4 pgs.
Bocco, Alessandra, et al., "Antioxidant Activity and Phenolic Composition of Citrus Peel and Seed Extracts", J. Agric. Food Chem, vol. 46, No. 6, (1998), 2123-2129.
Cardellina, John H., "The Adulteration of Commercial "Grapefruit Seed Extract" With Synthetic Antimicrobial and Disinfectant Compounds", HerbalGram Issue: 94 p. 62-66 2012; American Botanical Council, (2012), 62-66.
Castillo, J., et al., "Naringin and Neohesperidin Levels during Development of Leaves, Flower Buds, and Fruits of Citrus aurantium", Plant Physiology 99(1), (1992), 67-73.
Cushnie, T.P. Tim, et al., "Antimicrobial activity of flavonoids", International Journal of Antimicrobial Agents, 26 (2005), 343-356, (2005), 343-356.
Cvetnic, Acta Pham. 54, (2004), 243-250.
El-Ashiry, G. M., et al., "Local and Systemic Influences in Periodontal Disease", Int. Journal Vitamin Research, (1964), 202-218.
Hou, Joseph P, et al., "The Healing Powers of Chinese Herbs and Medicinal Recipes", Haworth Integrative Healing Press; ISBN:0789022028, (Apr. 27, 2005), 5 pgs.
Nogata, et al., "Flavonoid Composition of Fruit Tissues of Citrus Species", Already of record, submitting a clearer copy:, (2006), 15 pgs.
Nogata, Yoichi, et al., "Flavonoid Compositions of Fruit Tissues of Citrus Species", Biosci. Biotechnol. Biochem, 71, (1), 15 pgs.
Nogata, Youchi, et al., "Flavonoid Composition of Fruit Tissues of Citrus Species", Biosci. Biotechnol. Biochem., (Jan. 23, 2006), 178-192.
Rouseff, Russell, et al., "Quantitative Survey of Narirutin, Naringin, Hesperidin, and Neohesperidin in Citrus", Biosci. Biotechnol. Biochem., 71,(1), 4 pgs.
Von Woedtke, T., et al., "Aspects of the Antimicrobial Efficacy of Grapefruit Seed Extract and Its Relation to Preservative Substances Contained", Pharmazie Jun. 1999 ;54(6):452-6, (1999), Abstract.
Wollinsky, L. E., et al., "A Comparative Pilot Study of the Effects of a Dentifrice Containing Green Tea Bioflavonoids, Sanguinarine or Triclosan on Oral Bacterial Bioflim Formation", The Journal of Clinical Dentistry, vol. XI, No. 2, (2000), 53-59.

\* cited by examiner

COMBINATIONS FOR ORAL COMPOSITIONS, THEIR PREPARATION AND USE

RELATED APPLICATIONS

This application is a division of and claims the benefit of priority to U.S. application Ser. No. 12/374,443, filed Jan. 21, 2009, which is a national stage application under 35 U.S.C. § 371 of PCT/GB2007/002756, filed Jul. 20, 2007, and published as WO 2008/009956 A1, on Jan. 24, 2008, which claims priority to United Kingdom Application No. GB 06 14353.1, filed Jul. 20, 2006, which applications and publication are incorporated herein by reference and made a part hereof in their entirety, and the benefit of priority of each of which is claimed herein.

The present invention relates to flavonoid-containing compositions comprising the sodium salt of high molecular weight hyaluronic acid for use in the preparation of compositions, such as creams, gels, toothpastes, mouthwashes or dental rinses. In particular, it relates to compositions, preferably oral compositions, comprising an antibacterial bioflavonoid stock solution in combination with the sodium salt of high molecular weight hyaluronic acid, their preparation and use.

Certain compositions comprising flavonoids having antimicrobial, particularly antibacterial and especially anti-viral, activity are known. However, the term 'flavonoid' covers a large variety of differing compounds, which may be made available by extraction from various natural sources. Depending on both the source and the nature or method of extraction, the overall chemical composition of the resulting flavonoid mixture can itself vary widely. Individual flavonoids can vary greatly in their biological activity (or be inactive), both in terms of toxicity and effectiveness against microbes such as viruses and bacteria. Therefore, in combination, such flavonoids can also vary in their biological activity.

It has been found that it is possible to synergise, enhance or facilitate the biological activity of certain combinations of flavonoids by the addition of other agents to the flavonoid composition. Much effort has therefore been directed to finding a suitable combination of flavonoids, with or without other agent(s), that will have a desired effectiveness against certain microbes but without accompanying toxic or other disadvantageous effects in use. An example of such a combination is to be found in a combination of orange extracts, known as bioflavonoids, and natural fruit acids such as vitamin C, which is used in the poultry industry to kill food-related microbes such as *E coil* and *Salmonella*.

However, up until the present invention, it has not been proposed to use an orange-derived bioflavonoid/fruit acid combination in formulations for personal hygiene, such as oral, use. In particular, the known combination would be much too acidic for oral use. Furthermore, although it has been suggested that flavonoids be used in compositions such as toothpaste and mouthwash, these have either been unspecified as to their flavonoid components and/or limited to specific flavonoids. For example, patent specification no. WO 02/47615 discloses an oral composition comprising an organoleptically suitable carrier and a terpenoid and/or a flavonoid dispersed in the carrier; DE 19949575 discloses a combination of fluorides and flavonoids for treating dental disorders and preventing caries; and JP62051613 relates to a dentifrice composition containing 0.001-0.1 wt % flavonoid compound(s) selected from flavonol, chrysin, hesperetin and hesperidin. None of the prior art formulations disclose a combination of a bioflavonoid composition (itself comprising a particular combination of water-soluble flavonoid components) with one or more water-soluble fruit acid(s) in an amount and form suitable for oral administration as a solution, and having anti-bacterial activity.

Hyaluronic acid is the most important asulphurated mucopolysaccharide acid of the fundamental matter of the connective tissue, both from the strictly biochemical and from the physiological viewpoints. In man, hyaluronic acid is present not only in the connective tissue but also in the important biological fluids such as vitreous humor, aqueous humor, etc. and in the umbilical cord. It has practically zero toxicity, and specific contraindications for human use are not known.

As in the case of other components of natural substances, hyaluronic acid can be obtained by extraction from the relative natural substances, for example it can be extracted from chicken crests, or can be produced biotechnologically. Hyaluronic acid has a very wide range of molecular weights, which can vary from 30,000 to more than 15,000,000, depending on the type of process used. Said acid has been used in the form of its sodium salt for some time, both in human therapy and in cosmetic treatment.

In this respect the exogenous application of hyaluronic acid has a beneficial effect in favouring the connective organization, and in addition it opposes the inflammatory process induced by hyaluronidase-producing germs; it facilitates resolution of the phlogistic component, reduces abnormal capillary permeability, accelerates tissue repair processes and it performs an antiedematogenic action by metabolically binding free water to its molecular structures. The therapeutic indications for hyaluronic acid are numerous, including abrasive-excoriative dermatopathies, ulcers deriving from arteriosclerotic vasculopathies, varicose ulcers, cicatrization delays and surgical excisions.

It is known from EP 0,444,492 A1 that hyaluronic acid in sodium salt form and characterised by a molecular weight of between 800,000 and 4,000,000, preferably between 1,000,000 and 2,000,000, can be used as active principle in the preparation of pharmaceutical compositions for topical administration in the treatment and prophylaxis of inflammatory affections of the oral cavity and for cosmetic treatment and hygiene of the oral cavity.

Attempts to prepare formulations, particularly oral formulations, comprising hyaluronic acid and other other antibacterial agents, such as chlorhexidine have failed, with the resultant formulations being unstable. In some combinations it is necessary to use alcohol to prepare the formulation, which is generally undesirable. It has now been found that combinations of hyaluronic acid, in the form of its sodium salt, with bioflavonoids can be formulated for topical, preferably oral, use, and, in particular, the compositions do not require alcohol.

Without wishing to he bound by any particular theory, it is believed that the bioflavonoid mixture kills bacteria and viruses creating an optimal environment for the hyaluronic acid to improve and accelerate the rate of healing of the mucous and other inflamed tissues. Advantageously, all ingredients are naturally derived and no harsh or synthetic chemicals are used in the preparations.

Accordingly, the present invention provides a composition having a pH in the range of from 3 to 8.5, preferably 3.5 to 8, preferably 4 to 7, more preferably 5 to 6.5, comprising:
(a) in the range of from 0.1% to <10% w/w, based on the total weight of the composition, of a stock solution comprising a mixture of bioflavonoids and fruit acids or salts thereof;

(b) sodium hyaluronate; and
(c) water; and, optionally,
(d) a pharmaceutically acceptable carrier therefor;
wherein the sodium hyaluronate has an average molecular weight of between 800,000 and 4,000,000; and,
which may itself comprise (an)other pharmaceutically or pharmacologically acceptable ingredient(s) suitable for administration, preferably oral administration.

Preferably, the molecular weight of the sodium hyaluronate is between 800,000 and 4,000,000, and most preferably, between 1,000,000 and 2,000,000, such as 1,500,000. The compositions of the invention generally contain from 0.005% to 10% w/w, based on the total weight of the composition, of sodium hyaluronate.

The compositions according to the present invention for therapeutic use generally contain between 0.2 and 10% w/w, based on the total weight of the composition, and preferably between 0.2 and 1% wfw, of sodium hyaluronate, such as 0.4, 0.6 or 0.8%.

The compositions according to the present invention for oral cavity prophylactic, cosmetic and hygienic use contain between 0.005 and 0.1% w/w, based on the total weight of the oral composition, of sodium hyaluronate, such as 0.01, 0.02, 0.05 or 0.08%, and most preferably contain 0.01% w/w of sodium hyaluronate.

Preferably, the composition comprises in the range of from 0.1 to 5% w/w of the stock solution, more preferably from 0.1 to 2% w/w, such as about 1%. Suitably, the composition comprises in the range of from 20 to 80% w/w water, towards the lower end of that range in the case of a toothpaste and towards the upper end for a liquid composition such as a mouthwash/rinse/spray. For example, a paste may comprise in the range of from 20 to 45% w/w water, such as 20 to 30% w/w, particularly if silica is included in component (d), and a liquid formulation may comprise in the range of from 60 to 80% w/w water (all w/w based on the total weight of the composition).

Especially preferred is when the stock solution is preparable from, water-soluble bioflavonoids in combination with a fruit acid, such as citric, malic and ascorbic acids. One or more of the acids are preferably neutralized with a suitable base, such as a quaternary ammonium base, for example a choline base, such as choline carbonate, bicarbonate or, preferably, hydroxide. More preferably, citric, malic and ascorbic acids are all used in the preparation of the composition, and especially preferred is when these are fully neutralized to provide citrate, malate and/or ascorbate salts. Especially preferred is choline ascorbate. Accordingly, it is preferred that the stock solution is substantially free from fruit acids, by which is meant that its pH is around neutral. Exemplary pH ranges for the stock solution are from 3 to 8.5, 3.5 to 8.5, 3,5 to 8, 4 to 8, 4 to 7.5, 4.5 to 7.5, 4.5 to 7, 5 to 7, 5 to 6.5, 5.5 to 6.5 and 5.5 to 6, the pH being for example about 5, about 5.5, about 6, about 6.5 or about 7.

Without wishing to be bound by any particular theory, e present inventors believe that, as well as having a chelating effect on hard water, the fruit acids also synergise the biological activity of the active agents eg the bioflavonoids and choline ascorbate. Accordingly, a preferred stock solution comprises water-soluble bioflavonoids and choline ascorbate (present either as choline base (eg hydroxide) and ascorbic acid or as the salt per se).

The stock solution preferably further comprises a non-toxic solvent, such as a water-miscible or hydrophilic solvent, and more preferably comprises water and a water-miscible co-solvent such as glycerine, a polyhydric alcohol or the like. Especially preferred is when the solvent comprises a water/glycerine mixture, preferably in the ratio of from 2:1-1:2 (water:co-solvent). More preferably, components (c) and (d) (the balance comprising water, co-solvent(s) and excipient(s) and or/or carrier(s)) are alcohol-, especially ethanol-, free.

Accordingly, the stock solution preferably is preparable from:

| Ingredient | % (w/w) Ingredient in Stock Solution |
| --- | --- |
| Bioflavonoid mixture 45% in biomass) | 1-20, preferably 2 to 15, more preferably 3 to 15, such as 3, 4, or 15, most preferred is 3.3. |
| Citric acid | 1-20, preferably 4 to 15, such as 4, 5, 10, or 15, most preferred is 4.5. |
| Malic acid | 1-20, preferably 4 to 15, such as 4, 5, 10, or 15, most preferred is 4.5. |
| Ascorbic acid (vitamin C)* | 1-20, preferably 1 to 5*, such as 1, 2, 3, 4, or 5, most preferred is 1.5. |
| Choline hydroxide solution (45% in water)* | 1-45, preferably 4 to 20*, such as 5, 8, 10, 12, 15, or 18. |
| Glycerine/water or other solvent(s) | Balance, qv to 100%, preferably 5-50*, such as 7, 10, or 15, most preferred is 7.5. |

*Ascorbic acid and choline hydroxide (or other choline base) can be replaced by choline ascorbate, with amounts of glycerine and water (or alternative solvent(s)) increased appropriately. Preferred is when the solvent comprises approximately equal % of both glycerine and water, such as 5 to 25% each, such as 15% glycerine and 20% water (when choline is present as the hydroxide solution), or such as 25% glycerine and 25% water (when the choline and ascorbic acid are present as 5% choline ascorbate).

Accordingly, the compositions of the present invention preferably are preparable from (based on the weight of the composition):
(a) (i) in the range of from 0.0002-1.5% w/w bioflavonoids [excluding biomass, which preferably contributes another 0.00024-1.83% w/w];
(ii) in the range of from 0.001-2.0% w/w citric acid;
(iii) in the range of from 0.001-2.0% w/w malic acid;
(iv) in the range of from 0.001-2.0% w/w ascorbic acid;
(v) in the range of from 0.00045-2.03% w/w choline base; and
(b), (c) and (d) the balance comprising water, co-solvent(s) and excipient(s) and/or carrier(s).

More preferably, the compositions of the present invention are preparable from (based on the weight of the composition):
(a) (i) in the range of from 0.00045-0.9% w/w bioflavonoids [excluding biomass, which preferably contributes another 0.00055-1.1% w/w];
(ii) in the range of from 0.001-2.0% w/w citric acid;
(iii) in the range of from 0.001-2.0% w/w malic acid;
(iv) in the range of from 0.001-2.0% w/w ascorbic acid;
(v) in the range of from 0.00045-2.03% w/w choline base; and
(b), (c) and (d) the balance comprising water, co-solvent(s) and excipient(s) and/or carrier(s).

Since the stock solutions of the present invention therefore more preferably are preparable from the percentages given in the above-noted table, the compositions of the present invention more preferably are preparable from:
(a) (i) in the range of from 0.000675-0.675% w/w bioflavonoids [excluding biomas];
(ii) in the range of from 0.015-1.5% w/w citric acid;
(iii) in the range of from 0.015-1.5% w/w malic acid;
(iv) in the range of from 0.005-0.5% w/w ascorbic acid;
(v) in the range of from 0.015-0.9% w/w choline base; and
(b), (c) and (d) the balance comprising water, co-solvent(s) and excipient(s) and/or carrier(s).

Since preferred compositions of the present invention comprise in the order of 1% w/w of the stock solution, in one embodiment, preferred compositions of the invention are preparable from:
(a) (i) of the order of 0.0675% w/w bioflavonoids [excluding biomass];
(ii) of the order of 0.15% w/w citric acid;
(iii) of the order of 0.15% w/w malic acid;
(iv) of the order of 0.05% w/w ascorbic acid;
(v) of the order of 0.09% w/w choline base; and
(b), (c) and (d) the balance comprising water, co-solvent(s) and excipient(s) and/or carrier(s).

In another embodiment, most preferred compositions of the invention are preparable from:
(a) (i) of the order of 0.01485% w/w bioflavonoids [excluding biomass];
(ii) of the order of 0.045% w/w citric acid;
(iii) of the order of 0.045% w/w malic acid;
(iv) of the order of 0.015% w/w ascorbic acid; and
(b), (e) and (d) the balance comprising water, co-solvent(s) and excipient(s) and/or carrier(s).

In another embodiment, most preferred compositions of the invention are preparable from:
(a) (i) of the order of 0.01485% w/w bioflavonoids [excluding biomass],
(ii) of the order of 0.045% w/w citric acid;
(iii) of the order of 0.045% w/w malic acid;
(iv) of the order of 0.06% w/w choline ascorbate; and
(b), (c) and (d) the balance comprising water, co-solvent(s) and excipient(s) and/or carrier(s).

Preferably, the compositions of the invention are topical compositions. All compositions referred to herein are preferably in a form suitable for topical administration.

More preferably, the compositions of the invention are oral compositions. All compositions referred to herein are more preferably in a form suitable for oral administration.

The stock solution is prepared by processes known to those skilled in the art. Preferably, the co-solvents are mixed with the water at ambient temperature and then the acids involved in neutralization processes, such as ascorbic acid, are blended together with the solvent at an increased temperature, which is kept low enough to ensure no degradation of any of the ingredients. In the case of ascorbic acid, which thermally degrades above about 55 degC., the temperature is kept in the range of from about 25 to below 55 degC. and is preferably in the region of 50 degC. Preferably, the neutralization involves addition of choline hydroxide to ascorbic acid in the blend (starting pH=1.2; finishing pH=5.5-6.0), or choline ascorbate (ie wherein the ascorbic is already neutralized) itself can be added.

Then, the remaining acids (preferably, citric and malic) are added, followed by the bioflavonoids, resulting in a solution having a pH in the range of from about 2.0 to 6.5 but typically is from about 2.2 to 3.5, especially in the range of from 2.3 to 3.0. The remaining un-neutralised acids are also substantially neutralized, for example, by choline hydroxide, to result in a substantially neutral solution having a pH in the range of, for example, from 5 to 8.5, preferably 5.5 to 7, more preferably 5.5 to 6.5.

The stated antimicrobial effect of prior art formulations comprising a bioflavonoid relies on the inhibition by the bioflavonoid of the uptake of essential amino acids in the cytoplasmic membrane of the microbe, such as by inhibiting the viral neuroamidase. However, the formulations of the present invention are believed to be effective because the combination of selected soluble bioflavonoids with choline ascorbate results in encapsulation of the microbe, breakdown of the flavonone and glucoside components into independent fragments, and subsequent deactivation of the microbe by the flavonone fragments and choline ascorbate.

Preferably, the bioflavonoid mixture comprises water-soluble bioflavonoids in association with biomass resulting from the extraction process; accordingly, the bioflavonoid mixture may be associated with up to 40-60% w/w, preferably about 55% w/w, biomass (based on the weight of the bioflavonoid mixture). The bioflavonoids are preferably glucosides, especially those selected from isocriocirm, isonaringin, narangin, hesperidin, neohesperidin, neodiomin, naringenin, poncirin and rhiofolen, and more preferably each of these is present in the mixture. Especially preferred is when the major part of the bioflavonoid mixture comprises narangin and neohesperidin, such as when these comprise in excess of 75% of the bioflavonoid component (excluding biomass). Suitably, other bioflavonoids (such as flavonol, chrysin, hesperetin) are substantially absent from the bioflavonoid mixture and the bioflavonoid component therefore consists essentially of the water-soluble bioflavonoids listed hereinabove, although trace amounts of other bioflavonoids may be present. Especially preferred is when the water-soluble bioflavonoids comprise the following percentages (by weight of bioflavonoid in the total bioflavonoid component):

| Bioflavonoid | % of Total Bioflavonoid Component |
|---|---|
| Isocriocirm | 2.4 |
| Isonaringin | 2.7 |
| Narangin | 52.0 |
| Hesperidin | 3.1 |
| Neohesperidin | 27.8 |
| Neodiomin | 3.1 |
| Naringenin | 3.4 |
| Poncirin | 4.4 |
| Rhiofolen | 1.1 |
| Total | 100% |

A suitable source of such a water-soluble bioflavonoid mixture is herein referred to as 'HPLC 45', of which about 45% (of the total composition of HPLC 45) comprises such bioflavonoids, with the balance (about 55%) comprising biomass such as pectins, sugars and minor organic acids. As stated above, especially preferred is when the major part of the bioflavonoid mixture comprises narangin and neohesperidin, such as when these comprise in excess of 35% of the bioflavonoid component in a mixture with biomass such as HPLC 45. Accordingly, by weight of the total composition of HPLC 45, the following bioflavonoids are preferably present:

| Bioflavonoid | % in HPLC 45 (bioflavonoid component + biomass) |
|---|---|
| Neoeriocitrin | 1.1 |
| Isonaringin | 1.2 |
| Narangin | 23.4 |
| Hesperidin | 1.4 |
| Neohesperidin | 12.5 |
| Neodiomin | 1.4 |

| Bioflavonoid | % in HPLC 45 (bioflavonoid component + biomass) |
|---|---|
| Naringenin | 1.5 |
| Poncirin | 2.0 |
| Rhiofolen | 0.5 |
| Total | 45% of HPLC 45 |

The HPLC 45 is available from Exquim (the food arm of Grupo Ferrer) as Citrus Bioflavonoid Complex 45% HPLC. It is derived from a starting material comprised of the pith of immature, bitter (blood/red) oranges such as Seville oranges that are classed as 'inedible' and from which the pips, flesh and oily skin have been substantially removed or remain undeveloped. This starting material is crushed in a hydrophilic, ionic solvent such as water or water/alcohol mixtures, preferably water/ethanol in a ratio of about 1:10-20 (solvent: starting material). The resulting mixture is filtered to leave a water-soluble biomass, which is retained, and an insoluble biomass, which is discarded. The water-soluble biomass is then subject to fine filtration, after which it is flash-distilled to leave a brown, hygroscopic powder (HPLC 45).

Preferably, the bioflavonoid mixture for use in the compositions of the present invention is distinguishable particularly by comprising water-soluble glucosides from the mixture obtained from grapefruit or other citrus fruits or other plant sources, which comprise water-insoluble flavonoids; and, more preferably, is distinguishable from the mixture obtained when substantial amounts of the seeds, pulp and/or flesh of such fruits are comprised in the starting material, which particularly comprise water-insoluble components. Furthermore, the more developed/mature starting material of the prior art is more likely to have been subjected to pesticides and/or synthetic fertilizing media, and are therefore less 'organic' or pure in their origin than the bioflavonoid mixture of the solutions of the present invention.

Preferably, the stock solution comprises 1-20%, preferably 2 to 15%, more preferably 3 to 15%, such as 3, 4, or 15, most preferred is 3.3% w/w of the HPLC45. Accordingly, the stock solution preferably comprises 0.45-9%, preferably 0.9 to 6.75%, more preferably 1.35 to 6.75%, such as 1.35, 1.8, or 6.75, most preferred is 1.485% of the bioflavonoid mixture.

Preferably, the composition of the invention and, particularly in the absence of other ingredients except water, the stock solution, has a pH of from about 3 to about 8.5, more preferably of from about 4 to 7.5, such as about 5 to 7; especially preferred is when the pH is about 5.5 to 6.5. Most preferably, therefore, the composition is substantially free of hydrogen ions, such as from fruit acids; the fruit acids used in the preparation of the stock solution and/or composition therefore having been substantially neutralised, preferably as described above by addition of a base to the stock solution. On the other hand, when the composition also comprises a buffering agent, then the pH of the stock solution can vary outside these ranges provided that the buffering agent is present in an amount effective to provide the composition with a pH within these ranges.

Accordingly, component (d) of the compositions of this invention may comprise a buffering agent to regulate or adjust the pH of the final composition, such as an alkali metal hydroxide or ammonium hydroxide or a mono-, di- or tri-basic phosphate such as a tri(alkali metal) phosphate. Since the quantity of hydroxide is more difficult to measure than that of dibasic phosphate, it is preferred to use monobasic phosphates and dibasic phosphates. Another alternative is to use a combination of phosphoric acid with a dibasic or tribasic, such as tri(alkali metal), phosphate. The phosphates are preferably incorporated in the form of their sodium, potassium or ammonium salts; more preferably, sodium salts are employed. However, in cases where hypertensive effects of sodium ions are of concern, mono- and di-potassium phosphates may be used. When the buffering agent is disodium phosphate, for example, it may be present up to about 5% w/w of the composition, preferably in the range of from 0 to 0.5%, such as about 0.05% w/w.

Another optional ingredient, component (d), may comprise a source of fluoride, such as sodium fluoride or sodium monofluorophosphate, up to about 0.5% w/w of the compositions of the invention. The fluoride source is preferably in the range of from 0 to 0.15%, such as about 0.05% w/w in the case of liquid compositions but more in the case of toothpastes, where from 0 to 0.3%, such as around 0.24%, w/w or in the range of from 0 to 1500 ppm (as fluoride ions) is suitable.

Other additives may be present in the compositions of the invention, such as flavouring, sweetening or colouring agents, or preservatives. Mint, such as from peppermint or spearmint, cinnamon eucalyptus, citrus, cassia, anise and menthol are examples of suitable flavouring agents. Flavouring agents are preferably present in the oral compositions in an amount in the range of from 0 to 3%; preferably up to 2%, such as up to 0.5%, preferably around 0.2%, in the case of liquid compositions; but optionally more in the case of toothpaste, preferably 0.5 to 2%, more preferably around 1% w/w. Sweeteners include artificial or natural sweetening agents, such as sodium saccharin which may be present in an amount in the range of from 0 to 2%, preferably up to 1% w/w, such as 0.05 to 0.3% w/w of the oral composition. Colouring agents are suitable natural or synthetic colours, such as titanium dioxide or CI 42090, or mixtures thereof. Colouring agents are preferably present in the compositions in an amount in the range of from 0 to 3%; preferably up to 0.1%, such as up to 0.05%, preferably around 0.005-0.0005%, in the case of liquid compositions; but optionally more in the case of toothpaste, preferably up to 1%, more preferably around 0.5% w/w. Of the usual preservatives, sodium benzoate is preferred in concentrations insufficient substantially to alter the pH of the composition, otherwise the amount of buffering agent may need to be adjusted to arrive at the desired pH.

Other optional ingredients of component (d) may include other active agents such as anti-plaque agents and/or anti-microbial agents. Suitable agents include quaternary atnrmonium compounds such as domiphen bromide, cetyl pyridinium chloride (CPC), phenolic compounds, ethanol, and the preservatives mentioned above. Such active agents may be present in an amount in the range of from 0 to 4% w/w but may be as much as 70%, such as up to 30%, in the case of ethanol. For example, CPC or the like is preferably present up to 2%, such as about 0.05% w/w, especially in liquid compositions of the invention. Ethanol may comprise as much as 70%, preferably about 0 to 30% w/w in liquid compositions of the invention, such as about 15% w/w in a mouthspray, but preferred compositions of the invention, particularly oral compositions, are those wherein ethanol or any other alcohol is substantially absent.

Other optional ingredients of component (d) may include humectants, surfactants (non-ionic, cationic or amphoteric), thickeners, gums and binding agents. Suitable humectants include glycerine, xylitol, glycerol and glycols such as propylene glycol, which may be present in an amount of up to 50% w/w each, but total humectant is preferably not more than about 60-80% w/w of the composition. For example, liquid compositions may comprise up to about 30% glycerine plus up to about 5%, preferably about 2% w/w xylitol. Surfactants are preferably not anionic and may include polysorbate 20 or cocoamidobetaine or the like in an amount up to about 6%, preferably about 1.5 to 3%, w/w of the composition.

When the oral compositions of the invention are in the form of a mouthspray, it is preferred to include a film-forming agent up to about 3% w/w of the oral composition, such as in the range of from 0 to 0.1%, preferably about 0.001 to 0.01%, such as about 0.005% w/w of the oral composition. Suitable film-foimers include (in addition to sodium hyaluronate) those sold under the tradename Gantrez.

When the oral compositions of the invention are in the form of toothpaste, it is preferred to include gums, binders and/or thickeners, such as colloidal silica, carrageenan and cellulose derivatives such as sodium carboxymethylcellulose. Such ingredients may be present in an amount up to about 3% w/w of the oral composition, such as up to about 2%, preferably about 0.5 to 1%, w/w of the oral composition.

Toothpaste compositions of this invention may also comprise an abrasive agent, such as hydrated silica, dicalcium phosphate, or water-insoluble alkali metal metaphosphates, up to about 25% w/w and preferably in the range of from about 10 to about 15% w/w of the oral composition.

The compositions according to the present invention may be administered topically and be in the form of creams, gels, pastes, toothpastes and mouthwashes. In such cases, the pharmaceutical compositions according to the present invention generally contain conventional excipients, for example polyalcohols such as sorbitol and/or maltitol, glycols such as polyethyleneglycol, thickeners such as carboxymethylcellulose, preservatives such as methyl or propyl paraoxybenzoate, flavouring agents such as peppermint, sweeteners such as saccharin, and colouring agents.

The compositions of the present invention may be prepared by any method known in the art for the formulation of similar compositions, such as a toothpaste, mouthwash or rinse, mouthspray, or the like. All methods comprise bringing the components (a), (b) and (c) and, if present, (d) together in intimate physical admixture.

Preferably, the compositions are packaged in suitable packaging such as a plastics or metallic tube, plastics or glass transparent, translucent or opaque bottle, jar or dispenser, with or without spray or other applicator means, together with instructions for use. Such packaging may itself be further packaged into a cardboard box or other suitable container and the same or further instructions for use may be inserted therein or inscribed thereon; suitably, such instructions may be inscribed on a pack insert or leaflet. The packaging preferably lists the active, main or all ingredients of the composition. The instructions may include those known to the person skilled in the art of compositions, particularly those for anti-bacterial use. Accordingly, they may recommend that a pea-sized amount of toothpaste be applied to the dentition at regular intervals, 2-3 times per day; that a mouthful of mouthwash or rinse be sluiced around the oral cavity at least once per day and preferably after meals; and the like.

The oral compositions of the present invention may therefore be useful for treating, preventing or ameliorating the effects of a microbial, especially a bacterial, infection in the oral cavity or other periodontal disease; for cleaning, disinfecting or removing debris from the oral cavity; for refreshing, freshening, removing or improving the odour or taste in the oral cavity; and for generally attending to the hygiene, appearance and feel of the oral cavity. Accordingly, the present invention further provides a stock solution comprising a mixture of bioflavonoids and fruit acids (such as the mixture hereinbefore described) in combination with the sodium salt of high molecular weight hyaluronic acid, in the preparation of a medicament for the treatment of a microbial, especially a bacterial, infection in the oral cavity; in particular, wherein the medicament comprises in the range of from 0.1% to 10% w/w (based on the total weight of the oral composition) of the stock solution. Preferably, the present invention provides (a) a stock solution comprising a mixture of bioflavonoids and fruit acids together with (b) sodium hyaluronate; wherein the sodium hyaluronate has an average molecular weight of between 800,000 and 4,000,000, and (d) other pharmaceutically or pharmacologically acceptable ingredients suitable for oral administration (such as those described hereinbefore), in the preparation of a medicament for the treatment of a microbial, especially a bacterial, infection in the oral cavity; in particular, wherein the medicament comprises in the range of from 0.1% to 10% w/w (based on the total weight of the oral composition) of the stock solution.

The compositions according to the present invention for therapeutic use are advantageously used for gingival affections, characterised by inflammatory manifestations of the gingival tissue, such as gingivitis, stomatitis, irritations due to mechanical causes such as fixed or mobile prostheses or surgical operations etc. The gingival pastes according to the present invention can also be used during the dentition stage in children. The oral compositions of the present invention are useful for the treatment of mucositis, aphthous ulcers, lichen planus, oral *candida,* periodontitis or dry socket. The compositions of the present invention are useful for the treatment of infected, or potentially infected, and/or inflamed skin, such as acne, burns and wounds.

The compositions of the present invention are useful in the treatment or prevention of infections, disease or conditions arising from the following bacteria: *Actinomyces odontolyticus, Actinomyces viscosus, Porphyromonas gingivalis, Prevotella intermedia, Prevotella buccae, Prevotella dentalis, Streptococcus gordonii, Streptococcus sanguinis, S oralis, S sobrinus, S mutans, S intermedius, Lactobacillus acidophilus, Eubacterium nodatum, Actinomyces israelii, Actinornyces naeslundii, C albicans* and *C tropicalis.*

In biological tests, a stock solution (see Example 1) used in the preparation of the compositions of this invention was found to be inhibitory of all the above-mentioned bacteria at 1/10 dilution and the above-mentioned non-*Streptococcal* bacteria were also inhibited at 1/100 dilution. Other biological data are given in the Examples hereinbelow.

The present invention will now be illustrated by the following examples.

EXAMPLE 1

Preparation of Stock Solution (a) Preparation of HPLC 45

The starting material comprises the pith of immature, bitter (blood/red) oranges such as Seville oranges that are classed as 'inedible' and from which the pips, flesh and oily skin have been substantially removed. The starting material is milled and then crushed in water or water/ethanol in a ratio of about 1:10-20 (solvent: starting material). The resulting mixture is filtered to leave a water-soluble biomass, which is retained, and an insoluble biomass, which is discarded. The water-soluble biomass is then subject to fine filtration, after which it is flash-distilled to leave a brown, hygroscopic powder (HPLC 45). Alternatively, the HPLC 45 is available from Exquim (Grupo Ferrer).

(b) Bioflavonoid Composition of HPLC 45

Analysis of the HPLC 45 obtained in step (a) shows that 45% of the total composition of HPLC 45 comprises bioflavonoids, with the balance (55%) comprising pectins, sugars and minor organic acids. The percentage (by weight of bioflavonoids in the HPLC 45) of the following bioflavonoids are present:

| Bioflavonoid | % Bioflavonoids in HPLC 45 |
|---|---|
| Isocriocirm | 2.4 |
| Isonaringin | 2.7 |
| Narangin | 52.0 |
| Hesperidin | 3.1 |
| Neohesperidin | 27.8 |
| Neodiomin | 3.1 |
| Naringenin | 3.4 |
| Poncirin | 4.4 |
| Rhiofolen | 1.1 |
| Total | 100% |

Accordingly, by weight of the total composition of HPLC 45, the following bioflavonoids are present:

| Bioflavonoid | % HPLC 45 |
|---|---|
| Isocriocirm | 1.1 |
| Isonaringin | 1.2 |
| Narangin | 23.4 |
| Hesperidin | 1.4 |
| Neohesperidin | 12.5 |
| Neodiomin | 1.4 |
| Naringenin | 1.5 |
| Poncirin | 2.0 |
| Rhiofolen | 2.8 |

(c) Preparation of Stock Solution

| Ingredient | % Stock Solution |
|---|---|
| HPLC 45 | 15 |
| Citric acid | 15 |
| Malic acid | 15 |
| Ascorbic acid (vitamin C)* | 5* |
| Choline hydroxide solution (45% in water)* | 15* |
| Glycerine | 15* |
| Water | 20* |
| Total | 100% |

[*Ascorbic acid and choline hydroxide can be replaced by choline ascorbate 5%, with amounts of glycerine and water increased to 25% each]

The water, glycerine and ascorbic acid are blended together at ambient temperature and the temperature then increased to 50 degC. The choline hydroxide is added to neutralize the ascorbic acid (starting pH=1.2; finishing pH=5.5-6.0).

Then, the remaining acids (citric and malic) are added, followed by the HPLC 45, resulting in a stock solution having a pH of 6.2 to 7.2, and comprising 6.75% bioflavonoids (w/w of the stock solution).

EXAMPLE 2A

Mouthspray

| INGREDIENT | PERCENTAGE |
|---|---|
| Glycerine | 10.000 |
| Ethanol | 15.000 |
| Xylitol | 2.000 |
| Polysorbate 20 | 1.500 |
| Stock solution, pH adjusted to 6.44 | 1.000 |
| Flavour | 0.200 |
| Sodium Saccharin | 0.080 |
| Cetyl Pyridinium Chloride | 0.050 |
| Disodium Phosphate•12H$_2$O | 0.075 |
| Sodium Hyaluronate | 0.005 |
| Water | q.v. to 100% |

A. Laboratory Sample: A mouthspray according to the invention was prepared as follows, using the above-noted ingredients: In vessel (A) disperse the sodium hyaluronate in the water with stirring to give a lump free solution. Add the sodium saccharin, cetyl pyridinium chloride, disodium phosphate, xylitol and stock solution and stir until all the ingredients are fully dissolved. Add the glycerine and mix until homogeneous. In a separate vessel (B) combine the polysorbate 20, flavour and ethanol. Mix until the flavour is fully dispersed. Add the contents of vessel (B) to vessel (A) with stirring to give a homogeneous liquid.

B. Alternative (Production) Method: A mouthspray according to the invention may be prepared as follows, using the above-noted ingredients: In vessel (A) disperse the sodium hyaluronate in the glycerine. With stirring, add the water to give a lump free solution. Add the xylitol, stock solution, sodium saccharin, cetyl pyridinium chloride and disodium phosphate, and stir until all the ingredients are fully dissolved. In a separate vessel (B) combine the polysorbate 20, flavour and ethanol. Mix until the flavour is fully dispersed. Add the contents of vessel (B) to vessel (A) with stirring to give a homogeneous liquid.

EXAMPLE 2B

Mouthspray

| INGREDIENT | PERCENTAGE |
|---|---|
| Glycerine | 10.000 |
| Ethanol | 15.000 |
| Xylitol | 2.000 |
| Polysorbate 20 | 1.500 |
| Stock solution, pH adjusted to 6.44 | 1.000 |
| Flavour | 0.200 |
| Sodium Saccharin | 0.080 |
| Cetyl Pyridinium Chloride | 0.050 |
| Disodium Phosphate•12H$_2$O | 0.075 |
| Sodium Hyaluronate (average molecular weight 1,500,000) | 0.01 |
| Water | q.v. to 100% |

A mouthspray according to the invention may be prepared as above using the above-noted ingredients.

EXAMPLE 3

Mouthrinse

| INGREDIENT | PERCENTAGE |
| --- | --- |
| Glycerine | 25.000 |
| Ethanol | 0.000 |
| Xylitol | 2.000 |
| Polysorbate 20 | 1.500 |
| Stock solution (pH = 6.23 after 6 months at RTP) | 0.500 |
| Flavour | 0.200 |
| Sodium Saccharin | 0.050 |
| Sodium Fluoride | 0.050 |
| Disodium Phosphate•12H$_2$O | 0.050 |
| CI 18965 Yellow 2G) | 0.0009 |
| CI 42051 (Patent Blue V) | 0.0003 |
| Sodium Hyaluronate (average molecular weight 1,500,000) | 0.01 |
| Water q.v. to 100% | 70.53 |

A. Laboratory Sample: An oral rinse according to the invention may be prepared as follows, using the above-noted ingredients: In mixing vessel (A) disperse the sodium hyaluronate in the water with stirring to give a lump free solution. Add the sodium saccharin, sodium fluoride, disodium phosphate, colour(s), xylitol and stock solution and mix until all ingredients are fully dissolved. Add the glycerine and mix until homogeneous. In a separate vessel (B) combine the polysorbate 20 and flavour. Mix until the flavour is fully dispersed. Add the contents of vessel (B) to vessel (A) with stirring to give a homogeneous liquid.

B. Alternative (Production) Method: An oral rinse according to the invention may be prepared as follows, using the above-noted ingredients: In mixing vessel (A) disperse the sodium hyaluronate in the water with stirring to give a lump free solution. Add the humectant(s), stock solution, sodium saccharin, sodium fluoride, disodium phosphate and colour. Mix, until all ingredients are fully dissolved. In a separate vessel (B) combine the polysorbate 20, flavour and ethanol. Mix until the flavour is fully dispersed. Add the contents of vessel (B) to vessel (A) with stirring to give a homogeneous liquid.

EXAMPLE 4

Toothpaste

| INGREDIENT | PERCENTAGE |
| --- | --- |
| Glycerine | 30.000 |
| Hydrated Silica - abrasive | 12.000 |
| Hydrated Silica - thickening | 11.000 |
| Xylitol | 10.000 |
| Cocamidopropyl Betaine (30%) | 3.000 |
| Xanthan Gum | 1.000 |
| Stock solution (pH = 6.68 after 6 months at RTP) | 0.500 |
| Sodium Hyaluronate (average molecular weight 1,500,000) | 0.1 |
| Flavour | 1.000 |
| Sodium Saccharin | 0.260 |
| Sodium Fluoride | 0.240 |
| Titanium Dioxide | 0.500 |
| Water | to 100% |

A. Laboratory Sample: A toothpaste according to the invention may be prepared as follows, using the above-noted ingredients: In mixing vessel (A) disperse the sodium hyaluronate in the water with stirring to give a lump free solutiona and add the glycerine. To this add the sodium saccharin, sodium fluoride, stock solution and xylitol and stir to dissolve. Transfer the contents of vessel A to a vacuum mixer (vessel B). Preblend the powders (hydrated silicas, xanthan gum and titanium dioxide) in vessel C and add to the liquid phase in the vacuum mixer (B). Mix under vacuum until homogeneous. Add the surfactant and flavour to the vacuum mixer (B) and mix under vacuum to form a smooth paste.

EXAMPLE 5

Preparation of Stock Solution

The following stock solution was prepared as above:

| | |
| --- | --- |
| Bioflavonoid mix | 3.3% |
| Malic acid | 4.5% |
| Citric acid | 4.5% |
| Glycerin | 7.5% |
| Ascorbic acid | 1.5% |
| Water | 78.6% |
| Ph of solution | 1.5 to 1.75 |

EXAMPLE 6

Preparation of Stock Solution

The following stock solution was prepared as above:

| | |
| --- | --- |
| Bioflavonoid mix | 3.3% |
| Malic acid | 4.5% |
| Citric acid | 4.5% |
| Choline ascorbate | 6.0% |
| LFG61 alkyl glycoside | 13.3% |
| Propylene glycol | 7.5% |
| Water | 60.9% |
| Ph of solution | 1.5 to 1.75 |

Anti-Bacterial Activity

Tests to determine whether compositions of the invention are active against a range of anaerobes and facultative bacteria that are implicated in periodontal disease may be conducted as follows.

Method & Materials

Bacteria that may be used include *Actinomyces odontolyticus, Actinomyces viscosus, Porphyromonas gingivalis, Prevotella intermedia, Prevotella buccae, Prevotella dentalis, Streptococcus gordonii* and *Streptococcus sanguinis*, in particular ATCC-type strains. All the anaerobes may be grown in Fastidious Anaerobic Broth (FAB) at 37 degC. for 24 h in a Don Whitely Anaerobic Chamber (available from Don Whitely, Yorkshire, UK). The facultative bacteria may be grown in nutrient broth in 10% (v/v) carbon dioxide at 37 deg C. for 24 h. The starter culture is 1 ml of an overnight growth containing approximately $10^6$ cfu/ml. The cultures are supplemented with compositions of the invention in concentrations down to 1/10,000 (0.001%); the diluent being the appropriate broth. Growth may be estimated by a spectrophotometric increase in absorption at 650 nm.

Growth on 5% (v/v) blood agar plates may be used to assess the toothpaste and mouthwash compositions. Wells approximately 0.5 cm diameter may be cut in the agar and filled with dilutions of the respective composition; the diluent being the appropriate broth. The plates are pre-inoculated with approximately 0.2 ml of broth containing $10^6$ cfu/ml. The minimum inhibitory concentration may be taken as the well concentration were no inhibition of growth is seen.

Additional Tests

Two stock solutions were tested: Example 5 and Example 6. Ranges of two-fold dilutions were prepared for each formulation, having a pH of 1.75 and 2.0, respectively, using either Blood-Heart Infusion (BHI) or Sabouraud's broth as the diluent, giving solutions with a range of concentrations (8%-0.015625% Stock Solution, v/v).

Strains of several bacterial and candidal species (see Table 1) were obtained and cultured for 48 h under the appropriate conditions. Suspensions of each microorganism were prepared in broth (BHI broth for bacteria, Sabouraud's broth for *Candida* spp.) to a turbidity level approximately equal to MacFarland standard 3.0.

TABLE 1

Species of microorganism used in this study

| Aerobic bacteria | Anaerobic bacteria | Yeast |
| --- | --- | --- |
| Streptococcus gordonii | Actinomyces odontolyticus | Candida albicans |
| Streptococcus sanguinis | Actinomyces viscosus | Candida dubliniensis |
|  | Clostridium difficile | Candida glabrata |
|  | Porphyromonas gingivalis | Candida krusei |
|  | Prevotella buccae | Candida parapsilosis |
|  | Prevotella intermedia | Candida tropicalis |

A 100 μl-volume of each microbial suspension was added to the wells of a microtitre plate. An equal volume of the solution of either Example 5 or Example 6 (containing the matching broth) was added to each well, giving final concentrations of Stock Solution of 4%-0.0078125% (v/v). Wells were also prepared containing no Stock Solution and/or no microorganism, to act as controls. Each microtitre plate was incubated for 24 h at 37° C. under the appropriate atmospheric conditions. After incubation the relative amounts of each microbial species were estimated by measuring the turbidity in each well using a spectrophotometer reading absorbance at a wavelength of 544 nm. Absorbance readings were blanked using the controls with an absence of microorganisms.

The Minimal Inhibitory Concentration (MIC) was defined as the lowest concentration of Stock Solution that resulted in a significantly reduced amount of the microorganism >50% reduction) in comparison to the controls where the microorganism was grown in the absence of Stock Solution. Experiments were performed in triplicate and MICs were determined for the formulations of Example 5 and Example 6 in the presence of each microbial species.

Results:

The MIC values observed for the 13 microorganisms in response to both formulations of Example 5 and Example 6 are summarised below in Table 2.

The growth of each of the microorganisms studied was inhibited by both formulations of Example 5 and Example 6, with the exception of *Candida glabrata*. This yeast species' growth did not appear to be inhibited at all by Example 6 even when it was present at a concentration of 8% (v/v), the highest concentration used in this study.

Comparison of the MICs from the two formulations of Example 5 and Example 6 suggested that Example 5 was more effective than Example 6 at inhibiting microbial growth. The MIC for each microorganism was lower with Example 5 than Example 6, with the exception of *Porphyromonas gingivalis* for which both formulations had an equal value of 1%. Furthermore, Example 5 inhibited the growth of each microorganism when at a concentration of 1% (v/v), even if the reduction of growth was not quite >50% (the criterion set in this study to define the MIC). This supports the use of 1% (v/v) of the stock solution of Example 5 as the preferred working concentration in future products and research.

TABLE 2

MIC values observed in this study for each microorganism in response to the formulations of Example 5 and Example 6.

| | MIC (% Stock Solution, v/v) | |
| --- | --- | --- |
| Microorganism | Example 5 | Example 6 |
| *Actinomyces odontolyticus* | 0.015625 | 2 |
| *Actinomyces viscosus* | 2 | 4 |
| *Clostridium difficile* | 1 | 2 |
| *Porphyromonas gingivalis* | 1 | 1 |
| *Prevotella buccae* | 2 | 4 |
| *Prevotella intermedia* | 2 | 4 |
| *Streptococcus gordonii* | 0.03125 | 2 |
| *Streptococcus sanguinis* | 0.03125 | 2 |
| *Candida albicans* | 0.125 | 8 |
| *Candida glabrata* | 0.0625 | >8* |
| *Candida krusei* | 0.015625 | 2 |
| *Candida parapsilosis* | 0.03125 | 8 |
| *Candida tropicalis* | 0.0625 | 8 |

*No inhibition of growth apparent, even with highest concentration used in this study

The invention claimed is:

1. A method of treating infected, or potentially infected, and/or inflamed skin in a subject in need thereof which comprises topical application of an effective amount of a composition having a pH in the range of 3 to 8.5 comprising:
    (a) a mixture of (i) water soluble bioflavonoids comprising naringin and neohesperidin and (ii) fruit acids or salts thereof;
    (b) sodium hyaluronate of an average molecular weight between 800,000 and 4,000,000 Daltons;
    (c) water; and optionally
    (d) a pharmaceutically acceptable carrier,
    wherein the mixture of bioflavonoids is derived from the pith of immature bitter oranges.

2. The method according to claim 1 wherein the infected, or potentially infected, and/or inflamed skin, is acne, a burn or a wound.

3. The method according to claim 1 wherein the naringin and neohesperidin comprises in excess of 75% of the mixture of bioflavonoids.

4. The method according to claim 1 wherein the molecular weight of the sodium hyaluronate is between 1,000,000 and 2,000,000 Daltons.

5. The method according to claim 1 wherein the composition comprises 0.2 to 10% w/w of sodium hyaluronate.

6. The method according to claim 1 wherein the composition comprises 0.2 to 1% w/w of sodium hyaluronate.

7. The method according to claim 1 wherein the composition comprises 0.005 to 1% of sodium hyaluronate.

8. The method according to claim 1 wherein the composition comprises from 0.1 to 10% w/w based on the total weight of the composition of a solution comprising 0.45% to 9% of the mixture of bioflavonoids.

9. The method according to claim 1 wherein the fruit acid is citric acid.

10. The method according to claim 1 wherein the composition has a pH in the range of 4 to 7.

11. The method according to claim 1 wherein the composition has a pH in the range of 5 to 6.5.

12. The method according to claim 1 wherein the bioflavonoid mixture comprises from 40 to 60% w/w biomass, based on the weight of bioflavonoid mixture.

13. The method according to claim 1 wherein the composition is free of alcohol.

14. The method according to claim 1 for the treatment of infected skin.

15. The method according to claim 1 for the treatment of burns.

* * * * *